United States Patent
Chen et al.

(10) Patent No.: US 10,421,035 B2
(45) Date of Patent: Sep. 24, 2019

(54) METHOD AND DEVICE FOR PERFORMING PCO REACTION AND AIR PURIFIER COMPRISING THE DEVICE

(71) Applicant: KONINKLIJKE PHILIPS N.V., Eindhoven (NL)

(72) Inventors: Weizhong Chen, Eindhoven (NL); Haihui Wu, Eindhoven (NL); Ming Sun, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 15/106,848

(22) PCT Filed: Dec. 12, 2014

(86) PCT No.: PCT/EP2014/077612
§ 371 (c)(1),
(2) Date: Jun. 21, 2016

(87) PCT Pub. No.: WO2015/101472
PCT Pub. Date: Jul. 9, 2015

(65) Prior Publication Data
US 2017/0001139 A1    Jan. 5, 2017

(30) Foreign Application Priority Data
Dec. 30, 2013 (WO) ................. PCT/CN2013/001659
Jan. 14, 2014 (EP) ..................................... 14151016

(51) Int. Cl.
*B01D 53/00* (2006.01)
*A61L 9/20* (2006.01)
(Continued)

(52) U.S. Cl.
CPC ............ *B01D 53/007* (2013.01); *A61L 9/205* (2013.01); *B01D 51/10* (2013.01); *B01D 53/885* (2013.01);
(Continued)

(58) Field of Classification Search
CPC .... B01D 53/007; B01D 51/10; B01D 53/885; B01D 2259/4508; B01D 2257/708;
(Continued)

(56) References Cited

U.S. PATENT DOCUMENTS 5,835,840 A * 11/1998 Goswami .................. A61L 9/20
422/186.3
6,503,447 B1 * 1/2003 Mondjian .............. B01J 19/123
422/24
(Continued)

FOREIGN PATENT DOCUMENTS

| CN | 202056968 U | 11/2011 |
| CN | 202078854 U | 12/2011 |

(Continued)

OTHER PUBLICATIONS

Ting Guo, Ahipeng Bai, Can Wu and Tan Zhu, "Influence of environmental temperature and relative humidity on photocatalytic oxidation of toluene on activated carbon fibers coated TiO2", Front. Environ. Sci, Engin. China 2008, 2(2) 224-229.

*Primary Examiner* — Nicholas A Smith
*Assistant Examiner* — Colleen M Raphael

(57) ABSTRACT

The present invention relates to a method and a device for performing PCO reaction. The method comprises steps of: guiding an air flow into a PCO reactor, which PCO reactor contains photocatalyst for the PCO reaction; splitting the air flow into a first stream and a second stream, wherein quantity of the first stream being less than quantity of the second stream; obtaining the humidity of the photocatalyst;
(Continued)

controlling the humidity of the first stream according to the obtained humidity of the photocatalyst; adjusting the humidity of the photocatalyst by guiding the first stream to the photocatalyst; guiding the second stream through the photocatalyst; and illuminating the photocatalyst with light. By controlling the humidity of air passing through the photocatalyst oxidation based on the obtained humidity of the photocatalyst, PCO reaction can be performed effectively.

14 Claims, 3 Drawing Sheets

(51) Int. Cl.
  *B01D 53/88* (2006.01)
  *F24F 3/16* (2006.01)
  *B01D 51/10* (2006.01)
(52) U.S. Cl.
  CPC ........ *F24F 3/166* (2013.01); *B01D 2255/802* (2013.01); *B01D 2257/708* (2013.01); *B01D 2257/91* (2013.01); *B01D 2259/4508* (2013.01); *B01D 2259/804* (2013.01); *F24F 2003/1628* (2013.01); *F24F 2003/1667* (2013.01)
(58) Field of Classification Search
  CPC ........ B01D 2255/802; B01D 2259/804; B01D 2257/91; F24F 3/166; F24F 2003/1667; F24F 2003/1628; A61L 9/205
  USPC .......................... 204/157.3; 422/22, 24, 186
  See application file for complete search history.

(56) References Cited

U.S. PATENT DOCUMENTS

| | | | |
|---|---|---|---|
| 2003/0021720 A1 | 1/2003 | Reisfeld | |
| 2004/0040832 A1* | 3/2004 | Kartheuser | B01D 53/86 204/157.3 |
| 2005/0069471 A1* | 3/2005 | Obee | B01D 53/96 422/186.04 |
| 2005/0269254 A1* | 12/2005 | Roitman | B01D 53/86 422/24 |
| 2007/0041882 A1* | 2/2007 | Roseberry | A61L 9/205 422/186.3 |
| 2007/0181000 A1* | 8/2007 | Wilson | A61L 9/014 96/134 |
| 2009/0032390 A1* | 2/2009 | Osterlund | B01D 53/8687 204/157.3 |

FOREIGN PATENT DOCUMENTS

| | | |
|---|---|---|
| EP | 1600201 A1 | 11/2005 |
| EP | 1980317 A1 | 10/2008 |
| WO | 9709073 A1 | 3/1997 |
| WO | 2010093796 A1 | 8/2010 |
| WO | 2012118329 A2 | 9/2012 |

\* cited by examiner

METHOD AND DEVICE FOR PERFORMING PCO REACTION AND AIR PURIFIER COMPRISING THE DEVICE

This application is the U.S. National Phase application under 35 U.S.C. § 371 of International Application No. PCT/EP2014/077612, filed on Dec. 12, 2014, which claims the benefit of International Application No. 14151016.4 filed on Jan. 14, 2014 and International application PCT/CN2013/001659 filed Dec. 30, 2013. These applications are hereby incorporated by reference herein.

FIELD OF THE INVENTION

The invention relates to a method and a device for performing PCO reaction, in particular, to a method and a device for adjusting the humidity of a photocatalyst during PCO reaction. The invention further relates to an air purifier, which employs the device for performing PCO reaction.

BACKGROUND OF THE INVENTION

Indoor air quality has received immense attention since the early 1990s partially owing to the studies showing the level of pollutants in indoor environment is actually higher than in outdoor environment. In addition, people generally spend more than 80% of their time indoors, which contributes a higher risk from inhalation of pollutants than outdoors. In 1995, USEPA (US Environmental Protection Agency) identified that indoor air pollution was one of the top environmental risks. The indoor air pollutants may be categorized into three groups:

Gaseous pollutants and vapors that include volatile organic compounds (VOC) and inorganic compounds . . . ;

Particulate matters that include radioactive particles and environmental tobacco smokes . . . ; and Biological pollutants that include bacteria, fungi, virus . . .

Common methods of controlling indoor air pollution include controlling pollution sources, increasing the air exchange rate and using air purifiers. At present, the use of air purifiers becomes more popular to remove indoor air pollutants. Traditional air purifiers use filters to remove particulate matters or use sorption materials to adsorb gases or odors. However, these techniques only transfer the pollutants to another phase rather than removing the same, and additional disposal or handling steps are subsequently required. For instance, when an activated carbon filter is used to remove gaseous pollutants, the filter needs to be replaced quite frequently, which is costly and inconvenient to the consumers. An alternative remediation technology, which offers a number of advantages over conventional technologies, is the use of heterogeneous photocatalytic oxidation (PCO). PCO reaction can degrade various VOC pollutants into innocuous products such as $CO_2$ and $H_2O$ with lower power consumption.

The principle of PCO is illustrated in FIG. 1. PCO commonly uses semiconductor photocatalysts and ultraviolet (UV) light to decompose organic compounds into benign and odorless constituents such as water vapor ($H_2O$) and carbon dioxide ($CO_2$). When the photocatalyst is irradiated by UV light, electron in the valence band (VB) is excited to a vacant conduction band (CB), producing a positive hole ($h^+$) in the VB. The activation equation can be written as:

$$TiO_2 + hv \rightarrow h^+ e^- \qquad (1)$$

The positive holes ($h^+$) and electrons ($e$) are powerful oxidizing and reducing agents, respectively. They efficiently produce OH. (hydroxyl radical) and $O_2^-$ through the following reactions:

$$\text{Oxidation reaction: } h^+ + OH^- \rightarrow OH. \qquad (2)$$

$$\text{Reduction reaction: } e^- + O_{2ads} \rightarrow O^-_{2ads} \qquad (3)$$

OH. is a very powerful oxidizing substance. It is derived from the oxidation of adsorbed water or adsorbed $OH^-$. When OH. encounters VOCs in the air, the following degradation reaction takes place:

$$OH. + VOC + O_2 \rightarrow nCO_2 + mH_2O \qquad (4)$$

The main limiting factors of PCO include the incomplete oxidation and slow reaction rate, both will result in various byproducts, some of which could be toxic. Studies have shown that there is an optimum humidity range for achieving the best PCO result. When the humidity is too low, there could be insufficient water molecules for generating hydroxyl radicals; when the humidity is too high, water vapor competes with $TiO_2$ for adsorption sites, which decrease the rate of PCO. To improve reaction rate and minimize incomplete oxidation intermediates, humidity level at the surface of photocatalysts needs to be maintained in an optimum window. For instance, an optimum humidity range for removing toluene and formaldehyde by PCO could be about 1000 ppmv to 4000 ppmv, with TiO2 being the PCO catalyst.

WP97/09073A1 discloses a method and device for disinfecting an air stream containing microorganisms. Specifically, the air steam is provided with certain relative humidity e.g., greater than about 40% in view that PCO reaction requires that the relative humidity cannot be too low. However, WO97/09073 only mentioned generally the humidity of the air stream is controlled, without details regarding the implementation.

EP1980317A1 discloses a device for regaining deodoration function, esp., based on cold plasma. However, EP1980317A1 is not relating to photocatalytic oxidation of VOCs, and provides no disclosure of how the humidity of air flow is controlled.

WO2010/093796A1 discloses an air treatment device based on UV. Though WO2010/093796A1 mentions PCO reaction is dependent on relative humidity of the air, it only disclose a solution for designing the device according to certain relative humidity, or, adjust the parameters of the reaction system according to the given humidity, instead of changing the relative humidity of the air per se.

SUMMARY OF THE INVENTION

Humidity plays an important role in the decomposition of pollutants by the means of photocatalysis. Currently, there is no effective solution to control the humidity in a PCO reactor.

It might thus be advantageous to provide a method and a device for performing PCO reaction, in which the humidity of photocatalyst can be adjusted to a desired range.

For this purpose, an embodiment of the invention provides a method for performing PCO reaction, the method comprises steps of: guiding an air flow into a PCO reactor, which PCO reactor contains photocatalyst for the PCO reaction; splitting the air flow into a first stream and a second stream, wherein quantity of the first stream being less than quantity of the second stream; obtaining the humidity of the photocatalyst; controlling the humidity of the first stream according to the obtained humidity of the photocatalyst; adjusting the humidity of the photocatalyst by guiding the first stream to surface of the photocatalyst; guiding the second stream through the photocatalyst; and illuminating the photocatalyst with light.

By controlling the humidity of air passing through the photocatalyst oxidation based on the obtained humidity of the photocatalyst, PCO reaction can be performed effectively. The air flow is split and only a small part of the air flow is humidified/dehumidified when needed, so that the humidity of the photocatalyst can be adjusted to a desired range; moreover, the humidity of the air discharged can be kept unchanged, or, at least, will not be significantly changed.

In the context, "controlling the humidity of the first stream" refers to the functions of: humidifying the first stream, keeping the humidity of the first stream unchanged, or dehumidifying the first stream. Therefore, "adjusting the humidity of the photocatalyst" also refers to the functions of: humidifying the photocatalyst, keeping the humidity of the photocatalyst unchanged, or dehumidifying the photocatalyst.

Preferably, the step of controlling comprises modulating the humidity of the first stream to a target humidity according to a difference between the obtained humidity of the photocatalyst and a predetermined humidity of the photocatalyst.

By comparing the obtained humidity of the photocatalyst with a predetermined humidity of the photocatalyst, the humidity of the first stream can be controlled in a mode of direct feedback. That is, the adjustment amount of humidity for the first stream can be rectified automatically.

Preferably, the method further comprises detecting the humidity of the air flow; and the step of controlling comprises modulating the humidity of the first stream to a target humidity according to the obtained humidity of the photocatalyst, the detected humidity of the air flow and a predetermined humidity of the photocatalyst.

By detecting the humidity of the air flow, the adjustment amount of humidity for the first stream can be calculated based on the quantity of the first stream, so that the photocatalyst may receive a proper amount of humidity to achieve the optimum humidity.

In a preferred embodiment of the invention, in the step of controlling: the first stream is humidified if the obtained humidity of the photocatalyst is smaller than the predetermined humidity of the photocatalyst; the humidity of the first stream is kept unchanged if the obtained humidity of the photocatalyst is equal to the predetermined humidity of the photocatalyst; and the first stream is dehumidified if the obtained humidity of the photocatalyst is larger than the predetermined humidity of the photocatalyst.

Preferably, the humidity of the first stream is controlled by guiding the first stream through a humidity controlling channel; the humidity controlling channel comprises three channels in parallel, each of these three channels being respectively adapted for: humidifying the first stream, keeping the humidity of the first stream unchanged, or dehumidifying the first stream.

In another preferred embodiment of the invention, the PCO reactor comprises: an inner tube, which comprises a first opening and a second opening; the inner tube is perforated; the photocatalyst is arranged on the inner surface of the inner tube; an outer tube, which comprises a third opening and a fourth opening; the outer tube jackets the inner tube to form a jacket chamber comprising a jacket chamber opening between the first opening and the third opening; a sealing surface, which extends between the second opening and the fourth opening; and a light source, which is arranged within the inner tube for illuminating the photocatalyst.

Preferably, the first stream is guided into the jacket chamber from the jacket chamber opening after the step of controlling; the second stream is guided into the inner tube from the first opening.

The invention also proposes a device for performing PCO reaction, the device comprises: a PCO reactor, which contains photocatalyst for PCO reaction; an air flow channel for guiding an air flow for PCO reaction; an air splitting unit for splitting the air flow into a first stream and a second stream, wherein quantity of the first stream being less than quantity of the second stream; a hygrometer for obtaining the humidity of the photocatalyst; a humidity controlling channel for controlling the humidity of the first stream and adjusting the humidity of the photocatalyst by guiding the first stream to surface of the photocatalyst; and a main stream channel for guiding the second stream through the photocatalyst.

By splitting the air flow, only the humidity of the first stream is adjusted. PCO reaction can be performed effectively due to the optimum humidity of the photocatalyst. Moreover, the humidity of the discharged air can be kept unchanged, or, will not be significantly changed.

Preferably, the humidity of the first stream is controlled to a target humidity according to a difference between the obtained humidity of the photocatalyst and a predetermined humidity of the photocatalyst.

By comparing the obtained humidity of the photocatalyst with a predetermined humidity of the photocatalyst, the humidity of the first stream can be controlled in a mode of direct feedback. That is, the adjustment amount of humidity for the first stream can be rectified automatically.

Preferably, the device further comprises a humidity sensor for detecting the humidity of the air flow; and the humidity of the first stream is controlled to a target humidity according to the obtained humidity of the photocatalyst, the detected humidity of the air flow and a predetermined humidity of the photocatalyst.

By detecting the humidity of the air flow, the adjustment amount of humidity for the first stream can be calculated based on the quantity of the first stream, so that the photocatalyst may receive a proper amount of humidity to achieve an optimum humidity.

In a preferred embodiment of the invention, the first stream is humidified if the obtained humidity of the photocatalyst is smaller than the predetermined humidity of the photocatalyst; the humidity of the first stream is kept unchanged if the obtained humidity of the photocatalyst is equal to the predetermined humidity of the photocatalyst; and the first stream is dehumidified if the obtained humidity of the photocatalyst is larger than the predetermined humidity of the photocatalyst.

Preferably, the humidity controlling channel comprises three channels in parallel, each of these three channels being respectively adapted for: humidifying the first stream, keeping the humidity of the first stream unchanged, or dehumidifying the first stream.

In another preferred embodiment of the invention, the PCO reactor comprises: an inner tube, which comprises a first opening and a second opening; the inner tube is perforated; the photocatalyst is arranged on the inner surface of the inner tube; an outer tube, which comprises a third opening and a fourth opening; the outer tube jackets the inner tube to form a jacket chamber comprising a jacket chamber opening between the first opening and the third opening; a sealing surface, which extends between the second opening and the fourth opening; and a light source, which is arranged within the inner tube.

Preferably, the first stream is guided into the jacket chamber from the jacket chamber opening after the step of controlling; the second stream is guided into the inner tube from the first opening.

An air purifier comprising the device for performing PCO reaction according to any of the embodiments of the invention is also proposed.

These and other aspects of the invention will be apparent from and elucidated with reference to the embodiments described hereinafter. However, the invention is not limited to these exemplary embodiments.

BRIEF DESCRIPTION OF THE DRAWINGS

The present invention will now be described based on various embodiments with reference to the accompanying drawings, in which.

DETAILED DESCRIPTION OF THE INVENTION

Reference will now be made to embodiments of the disclosure, one or more examples of which are illustrated in the figures. The embodiments are provided by way of explanation of the disclosure, and are not meant as a limitation of the disclosure. For example, features illustrated or described as part of one embodiment may be used with another embodiment to yield still a further embodiment. It is intended that the disclosure encompass these and other modifications and variations as come within the scope and spirit of the disclosure.

Adjusting the humidity of the photocatalyst can be achieved by means of a relatively small part of the air flow, which is treated based on the obtained humidity of the photocatalyst. The small air stream is guided to the catalyst surface to have direct impact on the humidity level on the catalyst surface.

According to an embodiment of the invention, a method for performing PCO reaction comprises: guiding an air flow into a PCO reactor, which PCO reactor contains photocatalyst for the PCO reaction; splitting the air flow into a first stream and a second stream, wherein quantity of the first stream being less than quantity of the second stream; obtaining the humidity of the photocatalyst; controlling the humidity of the first stream according to the obtained humidity of the photocatalyst; adjusting the humidity of the photocatalyst by guiding the first stream to surface of the photocatalyst; guiding the second stream through the photocatalyst; and illuminating the photocatalyst with light.

Figure 1:
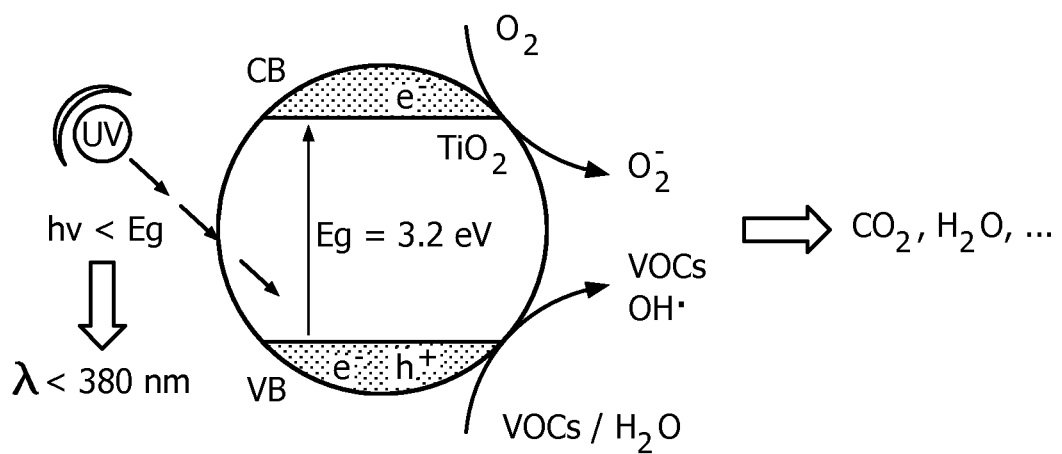
FIG. 1 illustrates the principle of photocatalytic oxidation.
Figure 2:
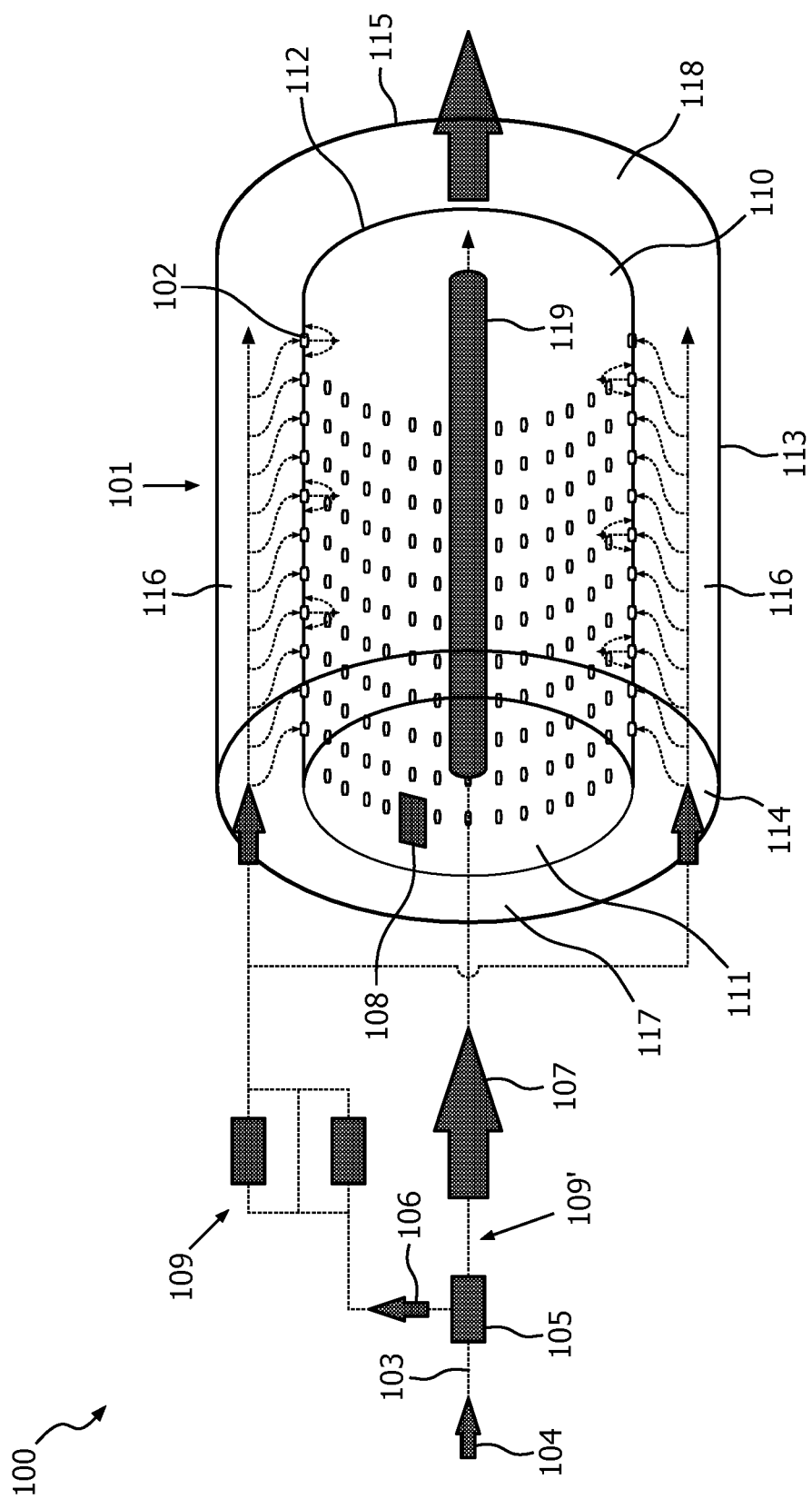
FIG. 2 illustrates a schematic diagram of a device for performing PCO reaction according to an embodiment of the invention.

According to an embodiment of the invention, the method can be carried out by a device for performing PCO reaction, which is shown in FIG. 2. The device 100 comprises: a PCO reactor 101, which contains photocatalyst 102 for PCO reaction; an air flow channel 103 for guiding an air flow 104 for PCO reaction; an air splitting unit 105 for splitting the air flow 104 into a first stream 106 and a second stream 107, wherein quantity of the first stream 106 being less than quantity of the second stream 107; an obtaining unit (e.g., hygrometer) 108 for obtaining the humidity of the photocatalyst 102; a humidity controlling channel 109 for controlling the humidity of the first stream 106 and adjusting the humidity of the photocatalyst 102 by guiding the first stream 106 to the photocatalyst 102; and a main stream channel 109' for guiding the second stream 107 through the photocatalyst 102.

In embodiments of the invention, the obtaining unit 108 can be implemented in any of following way:

a hygrometer that is adjacent to the surface of the photocatalyst 102 and configured to detect the humidity on the surface of the photocatalyst 102 directly; a hygrometer configured to detect the humidity of air flow 104 or the ambient air, the detected humidity is considered as the humidity of the photocatalyst;

a module that is able to communicate with an external source from where it obtains an estimation/forecast of the humidity of the photocatalyst (102).

Figure 3:
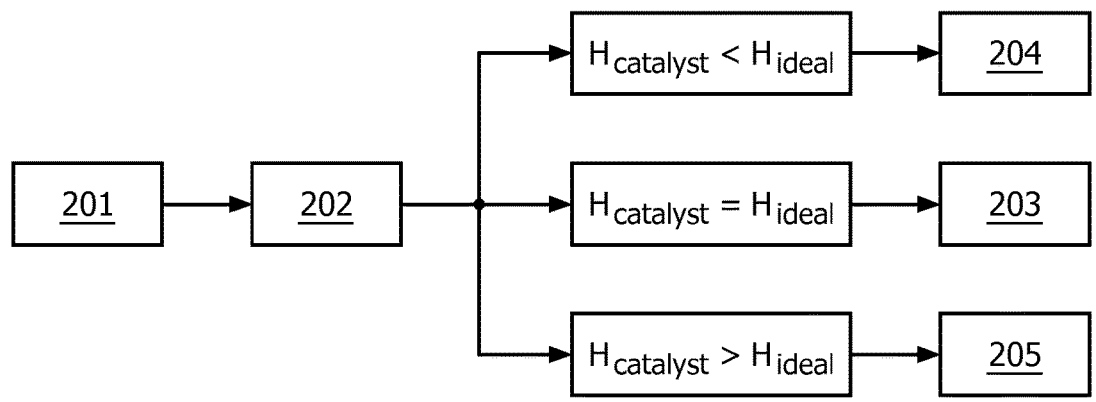
FIG. 3 illustrates a schematic diagram of operation principle according to an embodiment of the invention.

Typically, in an embodiment of the invention, the humidity adjustment of the photocatalyst 102 is implemented by changing the local humidity on the photocatalyst surface. As can be understood by those skilled in the art, a control unit (e.g., implemented by a processor or a control module) can be integrated into the humidity controlling channel 109 for the controlling. FIG. 3 illustrates a schematic diagram of operation principle according to an embodiment of the invention.

A humidity sensor detects (at 201) the humidity ($H_{catalyst}$) of the photocatalyst and sends (at 202) the result to a control unit. An ideal humidity value ($H_{ideal}$) is predetermined in advance. The humidity sensor does not have to be very accurate (e.g., 5% error margin is acceptable). As can be understood by those skilled in the art, at 201, the humidity of the photocatalyst can also be derived from some relevant parameters. For example, the humidity of the photocatalyst can also be derived from humidity in the PCO reactor.

The humidity of the first stream can be controlled by allowing the first stream pass through a desiccator/humidifier if the humidity of the first stream should be changed.

When $H_{catalyst}=H_{ideal}$ (or, in an optimum range), the humidity of the first stream is kept unchanged (at 203). In an alternative embodiment, all the air flow passes through the photocatalyst without splitting, and no pre-process is needed.

When $H_{catalyst}<H_{ideal}$, the humidification mode is activated (at 204). Based on the humidity difference, the control unit calculates the amount of the humidity adjustment according to the quantity/rate of the first stream passing through PCO reactor channel. The valve to the desiccator shuts off. The valve to the humidifier opens accordingly to allow the air pass through. A number of humidification methods are possible for the invention, e.g. passing through a water reservoir, piezo humidifier, heating a water tank, or spaying water to the air stream.

When $H_{catalyst}>H_{ideal}$, the dehumidification mode is activated (at 205). Based on the humidity difference, the control unit calculates the amount of the humidity adjustment according to the quantity/rate of the first stream passing through PCO reactor channel. The valve to the humidifier is shut off. The valve to the desiccator opens accordingly to allow the air pass through. A number of dehumidification methods are possible for the invention but passing through a desiccator is preferred.

It should be noted that: the amount of the humidity adjustment to the first stream can be adjusted if the quantity/rate of the first stream is constant; the quantity/rate of the first stream (i.e., the quantity proportion between the first and the second stream) can also be adjusted if the humidity adjustment to the first stream is constant; moreover, the humidity adjustment to the first stream and the quantity/rate of the first stream can both be adjustable.

In the context, the amount of the humidity adjustment refers to humidity variation caused by the humidity adjustment (i.e., the degree of the change in humidity, which is made to the first stream). The quantity of the first stream with respect to the air flow can thus be determined according to the amount of the humidity adjustment. Therefore, the quantity of the first stream can be adjusted to be relatively small if the amount of the humidity adjustment is large.

By controlling the humidity of air passing through the photocatalyst oxidation based on the obtained humidity of the photocatalyst, PCO reaction can be performed effectively. The air flow is split and only a small part of the air flow is treated, so that the humidity of the photocatalyst can be adjusted to a desired range; moreover, the humidity of the discharged air can be kept unchanged, or, will not be significantly changed.

After splitting the air flow, only a small part of the air flow (i.e., the first stream) is enough for achieving the optimum humidity of the photocatalyst. The hydroxyl radicals will be consumed by the mass air passing though the photocatalyst; and the consumed hydroxyl radicals will eventually generate $H_2O$, which can in turn be used by the photocatalyst for subsequent PCO reaction, not be discharged with the purified air. The VOC concentration is typically very low in air. Thus the water molecules generated by their degradation shouldn't change the ambient humidity significantly. Therefore, the discharged air (thus the ambient humidity) will be substantially unchanged.

Preferably, the humidity of the first stream is controlled to a target humidity according to a difference between the obtained humidity of the photocatalyst and a predetermined humidity of the photocatalyst.

By comparing the obtained humidity of the photocatalyst with a predetermined humidity of the photocatalyst, the humidity of the first stream can be controlled in a mode of direct feedback. That is, the adjustment amount of humidity for the first stream can be rectified automatically.

Preferably, the device further comprises a humidity sensor (not shown in FIG. 2) for detecting the humidity of the air flow; and the humidity of the first stream is controlled to a target humidity according to the obtained humidity of the photocatalyst, the detected humidity of the air flow and a predetermined humidity of the photocatalyst.

By detecting the humidity of the air flow, the adjustment amount of humidity for the first stream can be calculated based on the quantity of the first stream, so that the photocatalyst may receive a proper amount of humidity to achieve the optimum humidity.

In a preferred embodiment of the invention, the first stream is humidified if the obtained humidity of the photocatalyst is smaller than the predetermined humidity of the photocatalyst; the humidity of the first stream is kept unchanged if the obtained humidity of the photocatalyst is equal to the predetermined humidity of the photocatalyst; and the first stream is dehumidified if the obtained humidity of the photocatalyst is larger than the predetermined humidity of the photocatalyst.

With such a configuration, the humidity of the photocatalyst can be adjusted to a ideal value (or in an optimum range) without modifying the splitting structure for the air flow. Nevertheless, as described above, in an alternative embodiment, the entire air flow can also passes through the photocatalyst without splitting.

Preferably, the humidity of the first stream is controlled by guiding the first stream through the humidity controlling channel 109; the humidity controlling channel 109 comprises three channels in parallel, each of these three channels being respectively adapted for: humidifying the first stream, keeping the humidity of the first stream unchanged, or dehumidifying the first stream.

By arranging such three channels, the humidity of the first stream can be controlled in a switchable mode, which is operated according to the obtained humidity of the photocatalyst.

In another preferred embodiment of the invention, the PCO reactor comprises: an inner tube 110, which comprises a first opening 111 and a second opening 112; the inner tube 110 is perforated; the photocatalyst 102 is arranged on the inner surface of the inner tube 110; an outer tube 113, which comprises a third opening 114 and a fourth opening 115; the outer tube 113 jackets the inner tube 110 to form a jacket chamber 116 comprising a jacket chamber opening 117 between the first opening 111 and the third opening 114; a sealing surface 118, which extends between the second opening 112 and the fourth opening 115; and a light source 119, which is arranged within the inner tube 110 for illuminating the photocatalyst 102.

Preferably, the first stream 106 is guided into the jacket chamber 116 from the jacket chamber opening 117 after the humidity of the first stream 106 is controlled; the second stream 107 is guided into the inner tube 110 from the first opening 111.

The embodiment of the invention utilizes the incoming air flow to adjust the humidity in the vicinity of photocatalyst surface. Many photocatalysts can be the choice, e.g., $TiO_2$, surface modified $TiO_2$, $WO_3$, or hybrid of metal oxides. In addition, the inner tube 110 is perforated for flowing of the first stream. When the second stream 107 is mixed with the first stream 106 coming out of the tiny holes close to the photocatalyst, the humidity on the surface of the photocatalyst is changed without significant change to the overall humidity of the discharged air. The shape and structure of the PCO reactor 101 can also be varied.

In embodiments of the invention, there are typical ways which eventually change the humidity for the PCO reaction, which will be further described below: Output humidity of a humidifier/dehumidifier is controllable.

In such a case, to not impact the overall humidity of the ambient air, as described above, the quantity of the first stream 106 shall be small, e.g., 10% of the air flow 104. Assuming the target humidity for the PCO reaction is 4000 ppmv, and the humidity of the intake air is 2000 ppmv, the first stream 106 therefore needs to be humidified. As long as the output humidity of the humidifier is modulated to 4000 ppmv, the first stream 106 can be directed to the humidifier for humidification.

Output humidity from a humidifier/dehumidifier is relatively fixed.

The output humidity from a humidifier/dehumidifier is relatively fixed means, no matter how dry/wet the income air is, after pasting through the humidifier/dehumidifier, the outcome humidity of the air can be always around a certain value or within a certain range.

Assuming the flux of the total air flow 104 is 200 m³/h; the majority of the air flow (i.e., the second stream) will go through the main stream channel; and very small amount (e.g., <=20 m³/h) will be separated from the total air flow to form the first stream 104. Assume 20 m³/h is the flux guided to the surface of the photocatalyst 102, the optimum humidity $H_{ideal}$ is 4000 ppmv (predetermined). If the detected humidity (humidity of the ambient air) $H_{air}$ is 16000 ppmv, since $H_{air}>H_{ideal}$, the first steam 106 needs to be desiccated. The following algorithms can be used to determine how much air (i.e., the quantity of the first stream 104) needs to be desiccated. Assuming the humidity of the first stream 104 after passing though the desiccator is 1000 ppmv, then $$X \cdot 1000 + (20-X) \cdot 16000 = 20 \cdot 4000, \text{ hence, } X=16 \text{ m}^3/\text{h}.$$

Therefore, 16 m³/h of the total air flow needs to be desiccated. After being dried, 16 m³/h of the total air flow can be mixed with the rest untreated air (4 m³/h). The small stream of air (4000 ppmv, 20 m³/h) is guided to the catalyst surface.

Optionally, the ratio between the first stream and the second stream can also be adjusted according to the result of the calculating. That means, after calculating as described above, a stream with a flux of 16 m³/h can be separated directly from the total air as the first stream 106.

An air purifier comprising the device for performing PCO reaction according to any of the embodiments of the invention is also proposed. There can be a plurality of PCO reactors in one air purifier. The PCO reactors can also be connected with each other.

Those skilled in the art can understand that, the humidification/dehumidification of the catalyst 102 may not need to be repeated quite often. In some examples, the humidity control of the photocatalyst described in the context can be repeated once per hour or every two hours, or depending on the actual needs (e.g., the water on the catalyst volatilize too fast). Those skilled in the art can implement the invention to deal with those different scenarios without any additional considerable efforts.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for performing photocatalytic oxidation (PCO) reaction, the method comprises:
    guiding an air flow into a PCO reactor, said PCO reactor containing a photocatalyst;
    obtaining a humidity of the photocatalyst using a hygrometer;
    splitting the air flow into a first stream and a second stream dependent on the obtained humidity of the photocatalyst, wherein a quantity of the first stream being less than a quantity of the second stream;
    adjusting the humidity of the first stream to a target humidity according to the obtained humidity of the photocatalyst;
    adjusting the humidity of the photocatalyst by guiding the adjusted humidity first stream to the photocatalyst;
    guiding the second stream through the photocatalyst; and
    illuminating the photocatalyst with a light.

2. The method according to claim 1, wherein the step of adjusting comprises:
    modulating the humidity of the first stream to the target humidity according to a difference between the obtained humidity of the photocatalyst and a predetermined humidity of the photocatalyst.

3. The method according to claim 2, wherein in the step of adjusting:
    the first stream is humidified if the obtained humidity of the photocatalyst is lower than the predetermined humidity of the photocatalyst;
    the humidity of the first stream is kept unchanged if the obtained humidity of the photocatalyst is equal to the predetermined humidity of the photocatalyst; and
    the first stream is dehumidified if the obtained humidity of the photocatalyst is higher than the predetermined humidity of the photocatalyst.

4. The method according to claim 1, wherein the method further comprises:
    detecting the humidity of the air flow.

5. The method according to claim 1, wherein the humidity controlling channel comprises:
    a first channel is configured to humidify the first stream,
    a second channel configured to retain the humidity of the first stream, and
    a third channel configured to dehumidify the first stream.

6. A device for performing photocatalytic oxidation (PCO) reaction, the device comprises:
    a PCO reactor comprising:
        photocatalyst;
    an air flow channel configured to:
        guide an air flow into the PCO reactor for PCO reaction;
    a hygrometer configured to:
        obtain a humidity of the photocatalyst in the PCO reactor;
    an air splitting unit configured to:
        split the air flow into a first stream and a second stream dependent on the obtained humidity of the photocatalyst, wherein a quantity of the first stream being less than a quantity of the second stream, and;
    a humidity controlling channel configured to:
        adjust the humidity of the first stream to a target humidity according to the obtained humidity of the photocatalyst, and
        adjust the humidity of the photocatalyst by guiding the adjusted humidity first stream to the photocatalyst; and
    a main stream channel configured to
        guide the second stream through to the photocatalyst.

7. The device according to claim 6, wherein the humidity control channel is configured to:
    adjust the humidity of the first stream to the target humidity according to a difference between the obtained humidity of the photocatalyst and a predetermined humidity of the photocatalyst.

8. The device according to claim 7, wherein the humidity control channel is configured to:
    humidify the first stream when the obtained humidity of the photocatalyst is lower than the predetermined humidity of the photocatalyst;
    retain the humidity of the first stream when the obtained humidity of the photocatalyst is equal to the predetermined humidity of the photocatalyst; and
    de-humidify the first stream when the obtained humidity of the photocatalyst is higher than the predetermined humidity of the photocatalyst.

9. The device according to claim 6, wherein the device further comprises:
   a humidity sensor configured to detect the humidity of the air flow.
10. The device according to claim 6, wherein the humidity controlling channel comprises:
   a first channel configured to humidify the first stream;
   a second channel configured to retain the humidity of the first stream; and
   a third channel configured to dehumidify the first stream.
11. The device according to claim 6, wherein the PCO reactor comprises:
   an inner tube; comprising:
      a first opening, and
      a second opening, the inner tube being perforated, wherein the photocatalyst is arranged on an inner surface of the inner tube;
   an outer tube comprising:
      a third opening, and
      a fourth opening, the outer tube jacketing the inner tube to form a jacket chamber between the inner tube and the outer tube, the jacket chamber comprising a jacket chamber opening between the first opening and the third opening;
   a sealing surface extending between the second opening and the fourth opening; and
   a light source; arranged within the inner tube.
12. The device according to claim 11, wherein the first stream is guided into the jacket chamber and the second stream is guided into the inner tube from the first opening.
13. The device according to claim 6, wherein a quantity of the air flow in the first stream and a quantity of the air flow in the second stream is in a ratio dependent on the humidity of the photocatalyst.
14. An air purifier comprising:
   a PCO reactor device comprising:
      an air flow channel configured to:
         guide an air flow for PCO reaction;
      a hygrometer configured to:
         obtain a humidity of the photocatalyst;
      an air splitting unit configured to:
         split the air flow into a first stream and a second stream based on the obtained humidity of the photocatalyst, wherein a quantity of the first stream being less than a quantity of the second stream;
      a humidity controlling channel configured to:
         control the humidity of the first stream to a target humidity based on the obtained humidity of the photocatalyst, and
         adjust the humidity of the photocatalyst by guiding the adjusted humidity first stream to the photocatalyst; and
      a main stream channel configured to
         guide the second stream through the photocatalyst.

* * * * *